US007238349B1

(12) United States Patent
D'Hondt et al.

(10) Patent No.: US 7,238,349 B1
(45) Date of Patent: Jul. 3, 2007

(54) COMPOSITION

(75) Inventors: Erik D'Hondt, Merelbeke (BE); Norbert Hehme, Dresden (DE)

(73) Assignees: SmithKline Beecham Biologicals, s.a., Rixensart (BE); Saechsisches Serumwerk Dresden, Dresden (DE)

( * ) Notice: Subject to any disclaimer, the term of this patent is extended or adjusted under 35 U.S.C. 154(b) by 101 days.

(21) Appl. No.: 10/088,632

(22) PCT Filed: Sep. 27, 2000

(86) PCT No.: PCT/EP00/09509

§ 371 (c)(1), (2), (4) Date: Jul. 30, 2002

(87) PCT Pub. No.: WO01/22992

PCT Pub. Date: Apr. 5, 2001

(30) Foreign Application Priority Data

Sep. 30, 1999 (GB) ................................. 9923176.3

(51) Int. Cl. A61K 35/76 (2006.01)
(52) U.S. Cl. .................................................. 424/93.6
(58) Field of Classification Search ............ 424/209.1, 424/210.1, 206.1; 435/235.1, 239, 23
See application file for complete search history.

(56) References Cited

U.S. PATENT DOCUMENTS 5,149,531 A   9/1992   Youngner et al.
6,372,223 B1 * 4/2002   Kistner et al. ............ 424/209.1

FOREIGN PATENT DOCUMENTS

| EP | 0113 665 | 7/1984 |
|----|----------|--------|
| WO | WO 94/19013 | 9/1994 |
| WO | WO 95/22989 | 8/1995 |
| WO | WO 00/15251 | 3/2000 |
| WO | WO 00/47222 | 8/2000 |
| WO | 0015251 | * 3/2002 |

OTHER PUBLICATIONS

Couch et al (Journal of Infectious Diseases 176:S38-S44, 1997).*
Chaloupka et al (European Journal of Clinical Microbiology & Infectious Disease 15:121-127, 1996).*
Riberdy et al (Journal of Virology 73:1453-1459, 1999).*
Davenport et al (Journal of Immunology 100:1139-1140, 1968).*
Deliyannis et al (Vaccine 16:2058-2068, 1998).*
Kistner et al (Vaccine 16: 960-968, 1998).*
De Donato et al (Vaccine 17:3094-3131, Aug. 6, 1999).*
Palache et al (Vaccine 11:892-908, 1993).*
Brandon et al (Journal of Immunology 98:800-805, 1967).*
Montagne et al (Reviews of Infectious Diseases 5:723-727, 1978).*
Rimmelzwaan et al (Vaccine 17:1355-1358, Mar. 17, 1999).*
Rimmelzwaan et al (Vaccine 17:1355-1358, Mar. 1999).*
Enserink. Science 310:1889, 2005.*

MacKenzie. Tests dash hope of rapid production of bird flu vaccine. <<ww.newscientist.com/channel/health/bird-flu/dn8478>>, obtained from the internet Feb. 28, 2006.*
Gerdil. WHO meetiong on development and evaluation of influenza pandemic vaccines. <<www.who.int/entity/vaccine_research/diseases/influenza/Gerdil.pdf>>, obtained from the internet Feb. 28, 2006.*
Lin et al (Lancet 368:991-997, 2006; available online Sep. 7, 2006).*
Lu, et al., "A Mouse Model for the Evaluation of Pathogenesis and Immunity to Influenza A (H5N1) Viruses Isolated from Humans", *Journal of Virology*, 73(7): 5903-5911 (1999).
Guarnaccia, et al., "A Comparative Immunogenicity-Reactogenicity Dose-Response Study of Influenza Vaccine", *Annals of Allergy*, 65: 218-221 (1990).
Kistner, et al., "Development of a Vero Cell-Derived Influenza Whole Virus Vaccine", *Developments in Biological Standardization*, 98: 101-110 (1999).
Pressler, et al., "Comparison of the Antigenicity and Tolerance of an Influenza Aluminium Oxide Adsorbate Vaccine with an Aqueous Vaccine", *Pharmatherapeutica*, 3(3): 195-200.
Schenk, et al., "Antibody Formulation after Vaccination with Adsorbed and Non-Adsorbed A/New Jersey/8/76 Influenza Vaccines", *Pharmatherapeutica*, 3(3): 201-208 (1982).
Bresson, et al., "Safety and immunogenicity of an inactivated split-virion influenza A/Vietnam/1194/2004 (H5N1) vaccine: phase I randomized trial," *The Lancet*, vol. 367, pp. 1657-1664 (2006).
Hehme, et al., "Immunogenicity of a monovalent, aluminum-adjuvanted influenza whole virus vaccine for pandemic use," *Virus Research*, vol. 103, pp. 163-171 (2004).
Hehme, et al., "Pandemic preparedness: lessons learnt from H2N2 and H9N2 candidate vaccines," *Med. Microbiol. Immunol.*, vol. 191, pp. 203-208 (2002).
Treanor, et al., "Safety and immunogenicity of an inactivated subvirion influenza A (H5N1) vaccine," *The New England Journal of Medicine*, vol. 354, No. 13, pp. 1343-1351 (2006).
Boger, et al., "Subcutaneous and Intradermal Vaccination with Asian Influenza Vaccine," *J.A.M.A.*, 1957, 165(13):1687-1689.
Couch, et al., "Improvement of Inactivated Influenza Virus Vaccines," *The Journal of Infectious Diseases*, 1997, 176:S38-S44.
Hehme, N.W., "GSK's Pandemic Flu Vaccine Project: Evaluation of H2N2 and H9N2 Candidate Vaccines" GlaxoSmithKline Biologicals, *Who Meeting on Development and Evaluation of Influenza Pandemic Vaccines*, Geneva, 2005, pp. 1-20.

(Continued)

*Primary Examiner*—Bruce R. Campell
*Assistant Examiner*—Michelle Horning
(74) *Attorney, Agent, or Firm*—Elizabeth J. Hecht; Edward R. Gimmi; Charles M. Kinzig

(57) ABSTRACT

The invention provides a monovalent influenza vaccine comprising a low dose of egg-derived influenza virus antigen from an influenza virus strain that is associated with a pandemic outbreak or has the potential to be associated with a pandemic outbreak, in combination with an aluminium adjuvant. The invention also provides vaccine kits comprising a combination of a parenteral and a mucosal influenza vaccine, wherein the combined dose of antigen is no more than the conventional antigen dose. Also provided are methods for preparing the vaccines.

17 Claims, 2 Drawing Sheets

OTHER PUBLICATIONS

Figure 1:
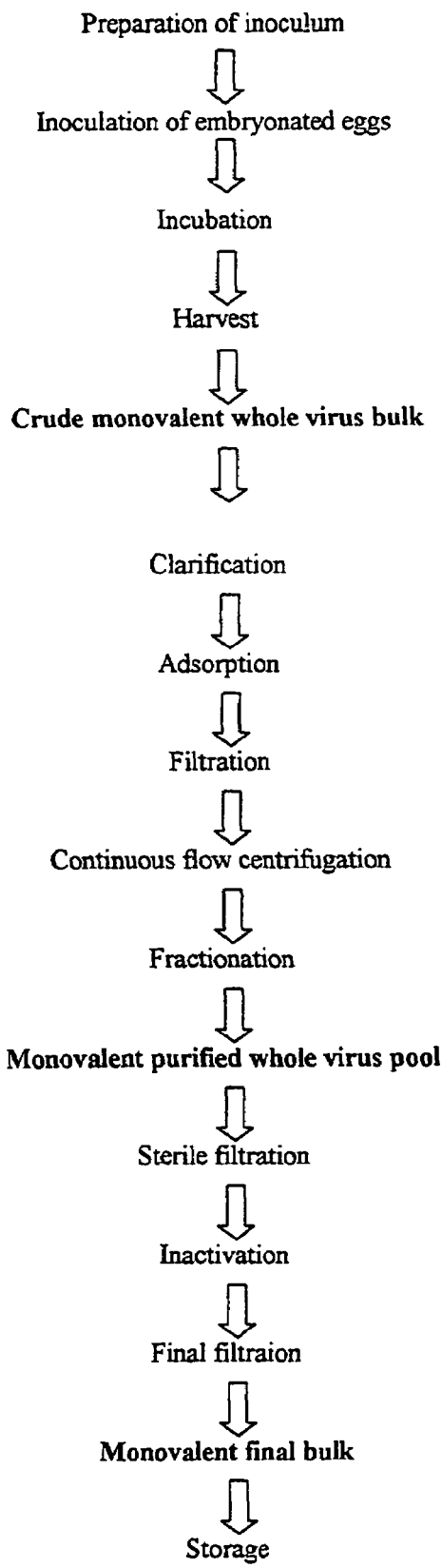
Figure 1:
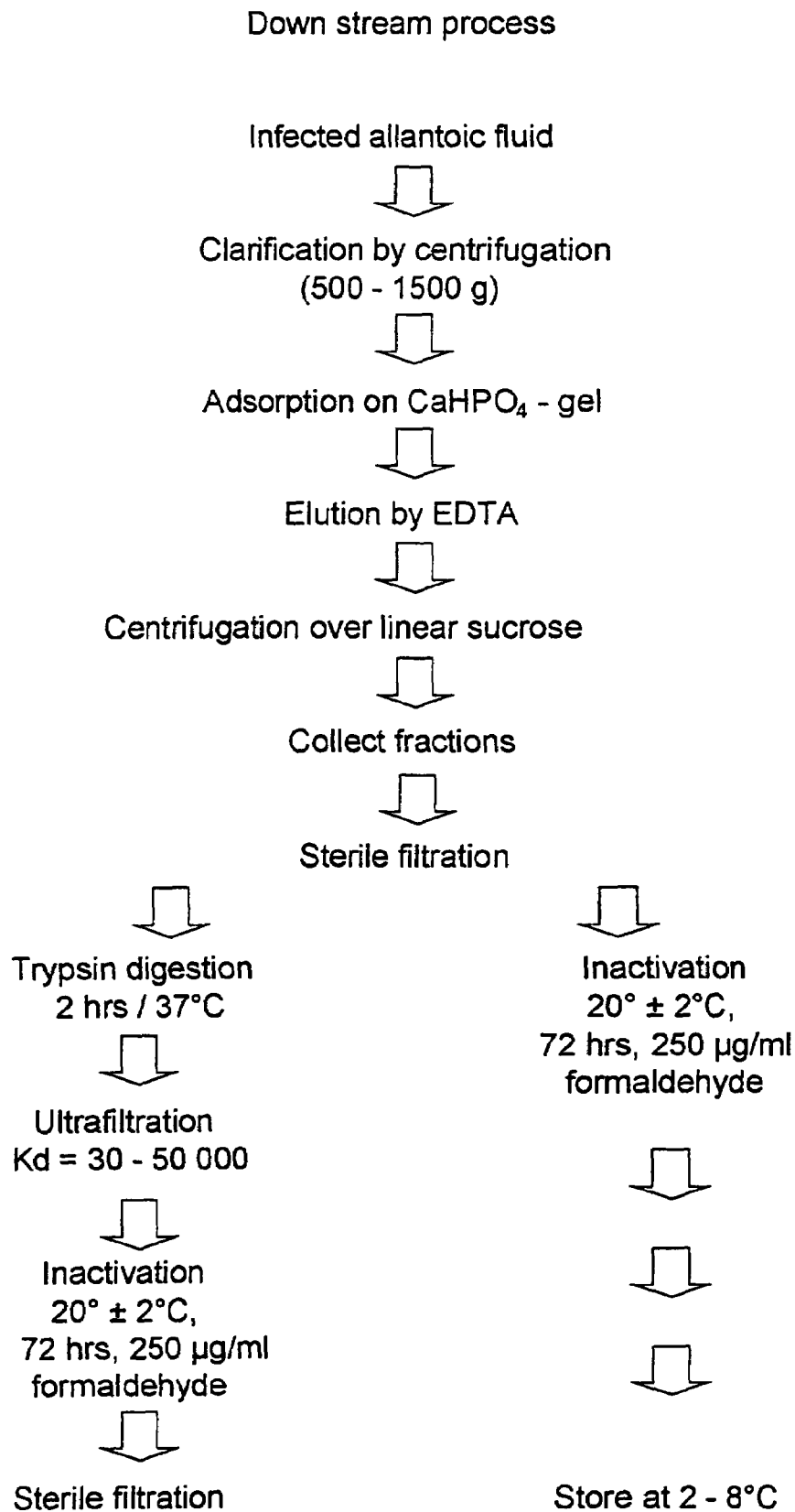

Kistner, et al., "Development of a Mammalian Cell (Vero) Derived Candidate Influenza Virus Vaccine," *Vaccine*, 1998, 16(9/10):960-968.

Kistner, et al., "Development of a Vero Cell-Derived Influenza Whole Virus Vaccine," *Developments in Biological Standardization*, 1999, 98:101-110.

La Montagne, et al., "Summary of Clinical Trials of Inactivated Influenza Vaccine," *Reviews of Infectious Diseases*, 1983, 5(4):723-736.

Lin, et al., "Safety and Immunogenicity of an Inactivated Adjuvanted Whole-Virion Influenza A (H5N1) Vaccine: A Phase I Randomised Controlled Trial," *The Lancet*, 2006, 368:991-997.

Merten, et al., "Production of Influenza Virus in Cell Cultures for Vaccine Preparation," *Advances in Experimental Medicine and Biology*, 1996, 397:141-151.

Offit, et al., "Addressing Parents' Concerns: Do Vaccines Contain Harmful Preservatives, Adjuvants, Additives, or Residuals?" *Pediatrics*, 2003, 112(6):1394-1401.

Rinella, et al., "Effect of Anions on Model Aluminum-Adjuvant-Containing Vaccines," *Journal of Colloid and Interface Science*, 1995, 172:121-130.

Seeber, et al., "Predicting the Absorption of Proteins by Aluminum-Containing Adjuvants," *Vaccine*, 1991, 9:201-203.

Shirodkar, et al., "Aluminum Compounds Used as Adjuvants in Vaccines," *Pharmaceutical Research*, 1990, 7(12):1282-1288.

Stephenson, et al., "Development of Vaccines Against Influenza H5," *The Lancet*, 2006, 6:458-460.

Stephenson, I., "H5N1 Vaccines: How Prepared are we for a Pandemic?" *The Lancet*, 2006, 368:965-966.

White, et al., Characterization of Aluminum-Containing Adjuvants, *Development Biology*, 2000, 103:217-228.

"Early Trial Show H5N1 Influenza Vaccine Safe and Effective in Humans at Low Doses," *The Lancet Press Release*, 2006.

\* cited by examiner

COMPOSITION

This is a 371 of International Application PCT/EP00/09509, filed Sep. 27, 2000, which claims benefit from the following Provisional Application: GB 9923176.3, filed Sep. 30, 1999.

This invention relates to novel vaccine formulations, methods for preparing them and their use in prophylaxis or therapy. In particular the present invention relates to vaccines for administration during pandemics.

Influenza virus is one of the most ubiquitous viruses present in the world, affecting both humans and livestock, following a still unpredictable pattern of regular epidemics and irregular pandemics.

Although it is often considered to be a trivial disease, influenza can have a devastating impact. Outbreaks have been recorded throughout history. Over 30 worldwide epidemics or pandemics, are known to have occurred since 1580, four of them in this century.

The usual symptoms of influenza include cough, fever, headache and muscle pains. Many sufferers develop complications or secondary bacterial infections which can be very serious and even fatal.

During inter-pandemic periods, influenza viruses circulate that are related to those from the preceding epidemic. The viruses spread among people with varying levels of immunity from infections earlier in life. Such circulation, over a period of usually 2–3 years, promotes the selection of new strains which have changed enough to cause an epidemic again among the general population; this process is termed "antigenic drift". "Drift variants" may have different impacts in different communities, regions, countries or continents in any one year, although over several years their overall impact is often similar.

Typical influenza epidemics cause increases in incidence of pneumonia and lower respiratory disease as witnessed by increased rates of hospitalisation or mortality. The elderly or those with underlying chronic diseases are most likely to experience such complications, but young infants also may suffer severe disease.

At unpredictable intervals, novel influenza viruses emerge with a key surface antigen, the haemagglutinin, of a totally different subtype from strains circulating the season before. This phenomenon is called "antigenic shift". It is thought that at least in the past pandemics have occurred when an influenza virus from a different species, such as an avian or a porcine influenza virus, has crossed the species barrier. If such viruses have the potential to spread from person to person, they may spread worldwide within a few months to a year, resulting in a pandemic.

The features of an influenza virus strain that give it the potential to cause a pandemic outbreak are: it contains a new haemagglutinin compared to the haemagglutinin in the currently circulating strains; it is capable of being transmitted horizontally in the human population; and it is pathogenic for humans. A new haemagglutinin may be one which has not been evident in the human population for an extended period of time, probably a number of decades, such as H2. Or it may be a haemagglutinin that has not been circulating in the human population before, for example H5, H9 or H6 which are found in birds. In either case the majority, or at least a large proportion of, or even the entire population has not previously encountered the antigen and is immunologically naïve to it.

H2N2 influenza viruses circulated between 1957 and 1968 when they were displaced by the H3N2 subtype which caused the last pandemic of the last century. Today people who have previously been exposed to H2N2 are likely to be are over thirty years of age. It has been suggested that an H2-containing virus might cause a new pandemic because a growing portion of the world population that was born after 1968 must be expected to be immunologically naïve. To investigate whether this theoretical dichotomy of the population regarding H2 immunity is a true fact, a sero-epidemiological study was conducted in 400 individuals and antibodies to H2 were measured.

This study was conducted in Germany and the antibody testing was carried out at Sächsische Serumwerk (Dresden, Germany), using a Haemagglutination Inhibition Test (HIT) specific for the H2 antigen. The titres are the reciprocal of the highest serum dilution that inhibits haemagglutination. The results confirm the immunologically naïve status of those under 30 years of age since only 7 out of 200 subjects had a measurable antibody titer in the low range of 10 to 20.

The data show furthermore that a significant proportion of those aged over 30 years is still seropositive for H2, 30 years or more after infection. The number of seropositives (HIT≧10) is 90%. In some of the serum samples anti-H2 titers (HIT) are as high as 640 and the geometric mean titer (GMT) for all seropositive study participants aged over 30 years was 65. An HIT≧40 is considered to be protective.

These observations confirm the possibility that an H2 virus could spread in the population under 30 years. Taking into account the current demographics and the fact that people younger than 30 years represent a large part of the world population, it is possible that an H2 virus could cause a pandemic again. This dichotomy in the world's population will further evolve over the years to come, increasing the pool of susceptible people.

Two years ago influenza with H5 (H5N1) which is an avian influenza virus was isolated from humans in Hong Kong. However the virus was not transmitted from person to person and so did not have the capability to cause a pandemic.

Certain parties are generally at an increased risk of becoming infected with influenza in a pandemic situation. The elderly, the chronically ill and small children are particularly susceptible but many young and apparently healthy people are also at risk. For H2 influenza, the part of the population born after 1968 are at an increased risk. It is important for these groups to be protected effectively as soon as possible and in a simple way.

Another group of people who are at increased risk are travelers. People travel more today than ever before and the regions where most new viruses emerge, China and South East Asia, have become popular travel destinations in recent years. This change in travel patterns enables new viruses to reach around the globe in a matter of weeks rather than months or years.

Thus for these groups of people there is a particular need for vaccination to protect against influenza in a pandemic situation or a potential pandemic situation.

A great deal of effort is being put into forming an effective international strategy for reacting to a pandemic situation and the World Health Organisation is instrumental in this. A key measure is the development of a pandemic vaccine strategy and up to now this has not been achieved on the scale required to address a flu pandemic.

It has now been surprisingly found that vaccines that will be useful in a pandemic situation can be formulated quickly and in a specific manner. In particular it has been discovered that a low dose influenza virus vaccine containing purified virus adjuvanted with a traditional carrier and/or formulated in a classical way, which can be produced quickly and economically enough to enable vaccination of populations on a large scale, is effective in humans.

In the past, crude preparations of egg-derived, whole inactivated influenza vaccine adjuvanted with aluminium salts have been used commercially. However, the product was poorly purified and rather reactogenic and the approach was abandoned at the end of the 1970s.

More recently, more highly purified, better characterised split influenza vaccines have been combined with adjuvants in an attempt to improve on the immunogenicity in adults and older people. In spite of significantly increased immune responses in mice, a number of approaches using new generation adjuvants could not be confirmed in man. In all of these studies, the regular 15 µg content of haemagglutinin antigen has been used to prepare the formulated vaccines.

A recent report (Kistner et al (1999) in *Inactivated Influenza Vaccines Prepared in Cell Culture, Dev Biol Stand. Basel, Karger.* Vol 98 pp 101–110) describes a primate study in which cell culture-derived vaccine containing three influenza strains mixed with $Al(OH)_3$ was given to chimpanzees. This induced a systemic response that was as good at a dose of 1.5 µg haemagglutinin per strain as at the standard 15 µg of haemaglutinin per strain. This study was directed towards the goal of developing a Vero cell-derived influenza whole virus vaccine which fulfills all the conventional requirements of the European Pharmacopoeia, the WHO and other regulatory organisations for an influenza virus vaccine.

For a standard influenza vaccine for routine use there may be difficulties associated with the use of aluminium salts as adjuvants. Influenza vaccines are intended for annual use and the repeated injections of $Al^{3+}$ may be undesirable. But for a pandemic situation that may occur only several times in a century, the use of $Al^{3+}$ is not precluded.

The present invention therefore provides in one aspect a vaccine composition comprising a low dose of influenza virus antigen from a single influenza virus strain that is associated with a pandemic outbreak or has the potential to be associated with a pandemic outbreak, in combination with a suitable adjuvant.

The vaccine of the present invention is provided at an effective dose to prevent influenza infection or to provide protection against influenza, in particular to provide protection against influenza morbidity or mortality.

The vaccine formulations of the present invention will preferably contain an immunoprotective quantity of the antigen. The vaccine formulations of the present invention may be prepared by conventional techniques.

The vaccine compositions of the invention may be administered in a single dose.

The use of a low dose of antigen and the use of a single influenza strain (i.e. a monovalent vaccine) contribute to the speed required to react to a pandemic situation.

A low dose of influenza virus antigen in the composition according to the invention is an amount of antigen which is below the currently accepted vaccine dose for human influenza vaccines which is 10–15 µg of haemagglutinin antigen per strain, normally 15 µg in accordance with regulations such as those issued by EMEA in Europe.

Alternatively, the vaccine compositions according to the invention are administered in more than one dose, particularly two doses, and preferably two doses administered simultaneously (on the same occasion) by different routes. Thus, the invention provides a two-dose regime which comprises the administration of both a systemic and a local (mucosal) vaccine, preferably simultaneously (or during a single visit). The administration of a mucosal vaccine as well as a parenteral vaccine enhances the immune response in particular the IgA antibody response, which contributes to protection from influenza infection.

In one preferred embodiment, vaccine compositions are administered both parenterally, for example intramuscularly, and via a mucosal route, particularly intranasally. In this embodiment, two different formulations will normally be required, that is a formulation for parenteral delivery and a formulation for mucosal delivery. These formulations may for example comprise different adjuvants and/or different amounts of antigen. Or they may simply comprise different volumes of liquid.

Thus, the present invention also provides a kit comprising at least the following two components:

(i) a low dose of influenza virus antigen formulated with an adjuvant suitable for parenteral administration; and (ii) a low dose of influenza virus antigen for mucosal administration, in a mucosal delivery device such as an intranasal spray device.

Intranasal spray delivery devices are commercially available, for example the bi-dose delivery device of Pfeiffer GmbH.

Such a two-route administration scheme will provide both a systemic immune response and a local immune response, the latter being preferably at the normal site of entry of the virus during infection (i.e. in the nasal mucosa).

Preferably, the combined antigen dose of the two components in this embodiment of the invention is less than the conventional 10–15 µg of haemagglutinin antigen per strain.

Thus, the low dose or the combined low dose according to the invention is generally below 10 µg of haemagglutinin, preferably below 8 µg of haemagglutinin, more preferably between 0.1 and 7.5 µg of haemagglutinin, most preferably between 1 and 5 µg of haemagglutinin per vaccine dose. Preferably the dose is significantly lower than in conventional influenza vaccines to enable the production of significantly greater quantities of influenza vaccine for a pandemic situation than would be possible using current influenza vaccine at current dose levels. Equally the dose of antigen needs to be high enough to provide sufficient protection.

Generally, the volume of vaccine according to the invention administered via a parenteral route such as intramuscularly will be about 0.5 ml and the volume of vaccine administered via a mucosal route such as intranasally will be a smaller volume, preferably about 0.2 ml e.g. 0.1 ml via each nostril.

The influenza virus antigen in the vaccine composition according to the invention needs to be obtainable by a quick and efficient method to meet the needs of a pandemic vaccine. Currently the preferred method is by growing influenza virus in eggs and purifying the harvested allantoic fluid. Eggs can be accumulated in large numbers at short notice. Cell culture methods, such as growth of the virus on dog kidney cell lines such as MDCK or MDCK-like cells, or on Vero cells, may also be suitable but are not preferred in the context of the present invention.

The influenza virus in the vaccine composition is preferably in the form of whole virus particles, but may alternatively be split virus prepared by conventional methods.

Split virus vaccine may be prepared by methods known in the art, such as the process described in patent no. DD 300 833 and DD 211 444, incorporated herein by reference. Traditionally split flu was produced using a solvent/detergent treatment, such as tri-n-butyl phosphate, or diethylether in combination with Tween™ (known as "Tween-ether" splitting) and this process is still used in some production facilities. Other splitting agents now employed include detergents or proteolytic enzymes or bile salts, for example sodium deoxycholate as described in patent no. DD 155 875, incorporated herein by reference. Detergents that can be used as splitting agents include cationic detergents e.g. cetyl trimethyl ammonium bromide (CTAB), other ionic detergents e.g. laurylsulfate, taurodeoxycholate, or non-ionic detergents such as Triton X-100 (for example in a process described in Lina et al, 2000, Biologicals 28, 95–103) and Triton N-101, or combinations of any two or more detergents.

However, an advantage of a whole virus vaccine over a split virus vaccine for a pandemic situation is that it avoids the uncertainty over whether a split virus vaccine can be successfully produced for a new strain of influenza virus. For some strains the conventional detergents used for producing the split virus can damage the virus and render it unusable. Although there is always the possibility to use different detergents and/or to develop a different process for producing a split vaccine, this would take time, which may not be available in a pandemic situation.

In addition to the greater degree of certainty with a whole virus approach, there is also a greater vaccine production capacity than for split virus since considerable amounts of antigen are lost during additional purification steps necessary for preparing a suitable split vaccine.

However, for a combination approach in which a vaccine is administered both intranasally and parenterally, a split vaccine may be preferred for the intranasal formulation while an inactivated whole virus vaccine may be preferred for the parenteral formulation.

Particularly preferred for the intranasal formulation is vaccine which has been inactivated or split and preferably contains non-ionic surfactants such as detergents selected from the octyl- or nonylphenoxy polyoxyethanols (for example the commercially available Triton™ series) and polyoxyethylene sorbitan esters (Tween™ series), particularly Triton X-100 or Tween 80 or a combination of both.

The detergents may be residual reagents left over from the splitting or purification process, and/or they may be added to the inactivated/split virus formulation or their concentrations adjusted.

Similarly, splitting agents such as cholic acid derivatives and in particular sodium deoxycholate (NaDOC), may be present in the vaccine compositions according to the invention, generally in trace amounts.

The use of an adjuvant in the vaccine composition according to the invention allows the use of a lower dose of virus antigen than in conventional vaccines.

Preferably the adjuvant in the composition according to the invention is an adjuvant which is readily available in large quantities. A particularly preferred adjuvant for the parentally administered vaccine according to the invention, contains at least one aluminium salt, most preferably a combination of aluminium hydroxide and aluminium phosphate. Preferably the aluminium phosphate is present at a higher concentration per vaccine dose than the aluminium hydroxide.

The total amount of aluminium salt per 0.5 or 1 ml dose of vaccine is normally in the range 0.1–2.0, preferably in the range 0.4–1.0 mg. Preferred is an adjuvant composition comprising aluminium phosphate and aluminium hydroxide, in which the amount of aluminium phosphate in relation to the amount of aluminium hydroxide is at least 2:1, more preferably 5:1 and at most preferably at least 8:1 or 9:1, by weight.

For a mucosally administered vaccine it is important to assure that the size of the viral antigens is adapted to mucosal penetration. This can be taken care of by the detergents or splitting agents already present in the formulation. Alternatively, or additionally, a suitable mucosal adjuvant known in the art may be employed, for example an absorption enhancing agent such as a polyoxyethylene ether or ester of general formula (I):

$$HO(CH_2CH_2O)_n\text{---}A\text{---}R \qquad (I)$$

wherein n is 1–50, A is a bond or —C(O)—, R is $C_{1\text{-}50}$ alkyl or phenyl $C_{1\text{-}50}$ alkyl.

Preferred surfactants falling within formula (I) are molecules in which n is 4–24, more preferably 6–12, and most preferably 9; the R component is $C_{1\text{-}50}$, preferably $C_4$–$C_{20}$ alkyl and most preferably $C_{12}$ alkyl. A particularly preferred example is polyoxyethylene-9-lauryl ether (laureth 9) which is described in the Merck index ($12^{th}$ ed: entry 7717, Merck & Co. Inc., Whitehouse Station, N.J., USA; ISBN 0911910-12-3). Laureth 9 is formed by reacting ethylene oxide with dodecyl alcohol, and has an average of nine ethylene oxide units.

In a further aspect, the invention provides a method for providing a priming immune response against an influenza virus in an unprimed individual or population which method comprises administering to the individual or population a low haemagglutinin vaccine or combined vaccine as described herein.

In another aspect the invention provides a method for the production of an influenza vaccine for a pandemic situation which method comprises admixing an influenza virus antigen from a single influenza virus strain that is associated with a pandemic outbreak or has the potential to be associated with a pandemic outbreak, with a suitable adjuvant and providing vaccine lots which contain less than 10 μg influenza haemagglutinin antigen per dose, or less than 10 μg per combined dose.

In still another aspect the invention provides a process for purifying influenza virus antigen for use in a vaccine, which process comprises the step of treating a mixture containing the influenza virus antigen with a protease to digest non-influenza virus proteins.

The purification is carried out on a preparation of influenza virus harvested from a culture. Surprisingly, the influenza virus particles are resistant to the protease digestion step. A preferred protease for use in the method is trypsin which is preferably used at a concentration of between 0.1–10 μg/ml pure trypsin. Alternative protease enzymes that may be used include plasmin and chymotrypsin.

Normally, the protease digestion step is performed after the influenza virus antigen has been partially purified by one or more physical separation steps such as centrifugation and filtration. Where the desired product is a whole virus vaccine, the protease digestion step is carried out prior to a virus inactivation step.

The purification method according to the invention can be successfully used to provide purified influenza virus antigen in the form of split or whole virus substantially free of contaminating host cell proteins, suitable for use in a vaccine.

The term "substantially free of contaminating host cell proteins" means that less than 10%, preferably less than 8% and more preferably less than 5% of the total protein is host cell protein as detected by scanning of Coomassie-stained polyacrylamide gels. In the case of influenza cultured in eggs, the predominant host protein is ovalbumin which makes up about 60–70% of the total protein mass of the allantoic fluid. Preferably ovalbumin is present in the purified influenza virus preparation at a concentration of less than 1%, more preferably less than 0.1% and most preferably only about 0.05% of the total protein content as assessed by scanning stained gels.

In a further aspect the invention provides the use of a dose or a combined dose of below 10 µg, or below 8 µg, or from 1–7.5 µg, or from 1–5 µg of influenza virus haemagglutinin antigen from a single strain of influenza associated with a pandemic outbreak or having the potential to be associated with a pandemic outbreak, in the manufacture of a vaccine for the prevention of influenza.

Alternative adjuvants which are suitable for use in the vaccine composition according to the invention include a range of adjuvants capable of enhancing the immune response to virus antigens.

3 De-O-acylated monophosphoryl lipid A (3D-MPL) is one such adjuvant. This is described for example in GB 2220211 (Ribi). Chemically it is a mixture of 3 De-O-acylated monophosphoryl lipid A with 4, 5 or 6 acylated chains and is manufactured by Ribi Immunochem Montana. A preferred form of 3 De-O-acylated monophosphoryl lipid A is disclosed in EP 0 689 454. The preferred form of 3D-MPL is particles of no greater than 120 nm, normally 60–120 nm, preferably about or less than 100 nm in diameter (as described in EP 0 689 454).

3D-MPL will usually be present in the range of 10 µg–100 µg, preferably 25–50 µg per dose wherein the antigen will typically be present in a range 2–50 µg per dose.

Another suitable adjuvant is QS21, which is an HPLC-purified, non-toxic fraction of a saponin from the bark of the South American tree Quillaja Saponaria Molina. Optionally this may be admixed with 3D-MPL, optionally together with an carrier.

A method for producing QS21 is described in U.S. Pat. No. 5,057,540.

Non-reactogenic adjuvant formulations containing QS21 are also suitable for use in the vaccine compositions according to the invention and are described for example in WO 96/33739. Such formulations comprising QS21 and cholesterol have been shown to be successful adjuvants when formulated together with an antigen.

Combinations of different adjuvants, such as those mentioned hereinabove, are also contemplated as providing an adjuvant which is suitable for use in the invention. For example, QS21 can be formulated together with 3D-MPL. The ratio of QS21: 3D-MPL will typically be in the order of 1:10 to 10:1; preferably 1:5 to 5:1 and often substantially 1:1. The preferred range for optimal synergy is 2.5:1 to 1:1 3D-MPL: QS21.

Advantageously the vaccine compositions according to the invention may be formulated with a carrier, usually in combination with one of the alternative adjuvants described above. The carrier may be for example an oil in water emulsion, or an aluminium salt.

A preferred oil-in-water emulsion comprises a metabolisible oil, such as squalene, alpha tocopherol and Tween 80. Additionally the oil in water emulsion may contain span 85 and/or lecithin.

In a preferred aspect aluminium hydroxide and/or aluminium phosphate will be added to the composition of the invention to enhance immunogenicity.

Typically for human administration QS21 and 3D-MPL will be present in a vaccine in the range of 1 µg–200 µg, such as 10–100 µg, preferably 10 µg–50 µg per dose. Typically the oil in water emulsion will comprise from 2 to 10% squalene, from 2 to 10% alpha tocopherol and from 0.3 to 3% Tween 80. Preferably the ratio of squalene to alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent alternative adjuvant formulation involving QS21, 3D-MPL and tocopherol in an oil in water emulsion is described in WO 95/17210.

The invention will now be further described in the following examples.

EXAMPLES

Example 1

Preparation of Monovalent Bulk for Whole Influenza Vaccine

The vaccine bulk was prepared according to the flow sheet shown in FIG. 1A. FIG. 1B shows a generalised flow sheet for the purification process, including the optional trypsin incubation step.

Production of Crude Monovalent Whole Virus

Preparation of Virus Inoculum

On the day of inoculation of embryonated eggs a fresh inoculum is prepared by mixing the working seed lot with a phosphate buffer containing gentamycin sulphate at 0.5 mg/ml and hydrocortison at 25 µg/ml. (virus strain-dependent)

The virus inoculum is kept at 2–8° C.

Inoculation of Embryonated Eggs

Nine to eleven day old embryonated eggs are used for virus replication.

The eggs are incubated at the farms before arrival at the manufacturing plant and transferred into the production rooms after decontamination of the shells.

The eggs are inoculated with 0.2 ml of the virus inoculum on an automatic egg inoculation apparatus.

The inoculated eggs are incubated at the appropriate temperature (virus strain-dependent) for 48 to 96 hours. At the end of the incubation period, the embryos are killed by cooling the eggs and stored for 12–60 hours at 2–8° C.

Harvest

The allantoic fluid from the chilled embryonated eggs is harvested by appropriate egg harvesting machines. Usually, 8 to 10 ml of crude allantoic fluid can be collected per egg. To the crude monovalent virus bulk 0.100 mg/ml thiomersal is added (in an alternative method, thiomersal is not added).

Concentration and Purification of Whole Virus from Allantoic Fluid

1. Clarification

The harvested allantoic fluid is clarified by moderate speed centrifugation (range: 4000–14000 g).

2. Adsorption Step

To obtain a $CaHPO_4$ gel in the clarified virus pool, 0.5 mmol/L $Na_2HPO_4$ and 0.5 mol/L $CaCl_2$ solutions are added to reach a final concentration of $CaHPO_4$ of 1.5 g to 3.5 g $CaHPO_4$/liter depending on the virus strain.

After sedimentation for at least 8 hours, the supernatant is removed and the sediment containing the influenza virus is resolubilised by addition of a 0.26 mol/L EDTA-Na$_2$ solution, dependent on the amount of CaHPO$_4$ used.

3. Filtration

The resuspended sediment is filtered on a 6 μm filter membrane.

4. Sucrose Gradient Centrifugation

The influenza virus is concentrated by isopycnic centrifugation in a linear sucrose gradient (0.55%). The flow rate is 8–15 liters/hour.

At the end of the centrifugation, the content of the rotor is recovered in three different fractions (the sucrose is measured in a refractometer):

| fraction 1 | 55-approximately 52% sucrose |
|---|---|
| fraction 2 | approximately 52*-26% sucrose |
| fraction 3 | 26-20% sucrose* | virus strain-dependent

Fraction 2 is diluted with phosphate buffer.

At this stage, the product is called "monovalent whole virus concentrate".

Sterile Filtration

The whole virus material is filtered on filter membranes ending with a 0.2 μm membrane. At the end of the filtration, the filters are washed with phosphate buffer. As a result, the final volume of the filtered fraction 2 is 5 times the original fraction volume.

Inactivation

The filtered monovalent material is diluted with phosphate buffer to reduce the total protein content to max. 250 μg/ml. Formaldehyde is added to a final concentration of 250 μg/ml and the inactivation takes place at 20° C.±2° C. for at least 72 hours.

Final Sterile Filtration

The protein concentration of the inactivated material is adjusted to approximately 500 μg/ml protein, prefiltered on membranes ending with 0.8 μm and finally filtered on membranes ending with 0.2 μm.

Depending on the virus strain the last filtration membrane can be 0.8 μm. At this stage, the product is called: "monovalent final bulk".

Storage

The monovalent final bulk is stored at 2–8° C. for a maximum of 18 months.

Purity

Purity was determined by O.D. scanning of Coomassie-stained polyacrylamide gels.

Peaks were determined manually. Results are given in the table below:

|  | Viral Proteins (HA, NP, M) % | | | | Other viral and host-cell derived proteins % |
|---|---|---|---|---|---|
|  | HA dimer | HA1 + 2 | NP | M |  |
| H3N2 |  |  |  |  |  |
| A/Syd/5/97 | 10.34 | 22.34 | 25.16 | 37.33 | 4.83 |
| A/Nan933/95 | 8.17 | 15.8 | 40.09 | 30.62 | 5.32 |

-continued

|  | Viral Proteins (HA, NP, M) % | | | | Other viral and host-cell derived proteins % |
|---|---|---|---|---|---|
|  | HA dimer | HA1 + 2 | NP | M |  |
| B |  |  |  |  |  |
| B/Har/7/94 | 5.71 | 24.07 | 15.64 | 50 | 4.58 |
| B/Yam/166/98 | 0.68 | 27.62 | 21.48 | 46.02 | 4.2 |
| H1N1 |  |  |  |  |  |
| A/Tex/36/91 |  | 33.42 | 24.46 | 34.33 | 7.79 |
| A/Bei/262/95 |  | 32.73 | 35.72 | 27.06 | 4.49 |
| H2N2 |  |  |  |  |  |
| A/sing/1/57 | 2.8 | 39.7 | 21.78 | 32.12 | 3.6 |

Alternative Method Involving Trypsin Step

Trypsin Digestion

After the sterile filtration step, the sterile material is subjected to a trypsinisation step. Pure trypsin for example commercially available pure porcine trypsin having a specific activity of 10,000 to 15,000 units/mg is added at a final concentration of 0.1–10 μg/ml. The mixture is incubated for 2 hrs at 37° C., stirring gently. The material is then refrigerated to cool for further processing.

Ultrafiltration

After trypsin digestion, the material may be subjected to ultrafiltration either before or after inactivation (as described above).

The virus material is ultrafiltrated on membranes with a mean exclusion limit of 20,000 to 50,000 D. During ultrafiltration, the content of formaldehyde and sucrose is considerably reduced.

After a first 4 fold volume reduction the volume remains constant during ultrafiltration (diafiltration) by adding phosphate buffer and phosphate buffered saline.

Results

Influenza whole virus vaccine prepared according to the trypsin method was analyzed on Coomassie-stained polyacrylamide gels. The viral proteins migrated to the same position as viral proteins which had not undergone a trypsin digestion step, indicating that the viral proteins had not been protease digested.

Example 2

Preparation of Vaccine Doses from Bulk Vaccine

Final vaccine is prepared by mixing final bulk vaccine prepared as described in Example, with adjuvant mix and final buffer in such a way that the targeted antigen content is obtained and a concentration of 0.5 mg of Al salts is achieved per dose. The buffer used contains several salts, as listed below. The adjuvant is a mix of AlPO$_4$ and Al(OH)$_3$ and is used in a proportion of 3.6 mg of AlPO$_4$ and 0.4 mg of Al(OH)$_3$ per 4 mg/ml of stock solution.

Buffer composition:

| Distilled water | 0,800 l |
|---|---|
| NaCl | 7,699 g |
| KCl | 0,200 g |
| MgCl$_2$•6H$_2$O | 0,100 g |
| Na$_2$HPO$_4$•12H$_2$O | 2,600 g |
| KH$_2$PO$_4$ | 0,373 g | made up to a final volume of 1 liter with distilled water.

The procedure is as follows:
1. Use adjuvant mix at 10–15° C.
2. Add final vaccine buffer at 15–20° C. and gently mix with magnetic stirrer.
3. While mixing add the appropriate bulk vaccine at 5–10° C.
4. Continue mixing for 10 to 30 minutes at room temperature.
5. Move adsorbed vaccine to cold room waiting for filling.
6. Final vaccine volume is 0.5 ml per dose.

Example 3

Clinical Data—Low Dose Split Influenza Vaccine Adjuvanted with Aluminium Salts

The following data come from a clinical trial in which a trivalent flu vaccine was prepared according to the general manufacturing outline for the commercially available Fluarix (Trade Mark) vaccine (which is a split flu vaccine). In practice, final trivalent bulk material was mixed with aluminium adjuvant as described in Example 2. Several different HA dosages were prepared.

The vaccine lots were tested in two age populations, 18–60 years and >60 years, at 1.8 µg per dose per strain and 3.75 µg per dose per strain. 50 volunteers were vaccinated in each group.

The data corresponding to doses of 1.8 and 3.75 µg per strain are presented in the tables below.

Haemagglutination Inhibition (HAI) Activity of Flu-Specific Serum Abs

Sera (50 µl) are treated with 200 µl RDE (receptor destroying enzyme) for 16 hours at 37° C. The reaction is stopped with 150 µl 2.5% Na citrate and the sera are inactivated at 56° C. for 30 min. A dilution 1:10 is prepared by adding 100 µl PBS. Then, a 2-fold dilution series is prepared in 96 well plates (V-bottom) by diluting 25 µl serum (1:10) with 25 µl PBS. 25 µl of the reference antigens are added to each well at a concentration of 4 hemagglutinating units per 25 µl. Antigen and antiserum dilution are mixed using a microtiter plate shaker and incubated for 60 minutes at room temperature. 50 µl chicken red blood cells (RBC) (0.5%) are then added and the RBCs are allowed to sediment for 1 hour at RT. The HAI titre corresponds to the inverse of the last serum dilution that completely inhibits the virus-induced hemagglutination.

|  | ADSORBED VACCINE 3.75 µG/DOSE/STRAIN | | | ADSORBED VACCINE 1.8 µG/DOSE/STRAIN | | |
|---|---|---|---|---|---|---|
|  | H1N1 | H3N2 | B | H1N1 | H3N2 | B |
| Seroconversion factor | | | | | | |
| <60 y | 5 | 4.2 | 2.8 | 3.5 | 3.6 | 2.0 |
| >60 y | 3.1 | 3.2 | 1.6 | 2.5 | 3.0 | 1.8 |
| Seroconversion rate % | | | | | | |
| <60 y | 57 | 5.5 | 28 | 51 | 45 | 24 |
| >60 y | 44 | 4.4 | 13 | 38 | 38 | 13 |
| Protection rate % | | | | | | |
| <60 y | 89 | 87 | 100 | 82 | 76 | 98 |
| >60 y | 81 | 71 | 100 | 64 | 67 | 100 |

| PROTECTIVE RATES (%) IN 18–60 YEAR AGE GROUPS | | | | |
|---|---|---|---|---|
|  | 3.75 µg/dose/strain | | 1.8 µg/dose/strain | |
|  | Pre | Post | Pre | Post |
| Against H1N1 | 43 | 89 | 45 | 82 |
| Against H3N2 | 40 | 87 | 24 | 76 |
| Against B | 85 | 100 | 82 | 98 |

EU criteria for the group 18–60 y are as follows:
  Seroconversion factor >2,5
  Seroconversion rate >40%
  Protection rate after vaccination >70%
  From the data in the tables it can be concluded that the EU criteria for seroconversion factor, seroconversion rate and protection rate are exceeded in the 2 age populations for the two different dosages tested against the A strains of influenza.

The protection rates against the B virus were over 80 and 90% before vaccination in the two study groups respectively. This pre-vaccination seropositivity to the B strain affects the vaccine response negatively. In spite of this, the antibodies to the B strain doubled after vaccination resulting a close to 100% protection rate.

Thus, a vaccine formulated with less than 4 µg of HA per strain and aluminium adjuvant has an acceptable reactogenicity profile (data not shown) and can induce an immune response that is in full compliance with all three EU criteria in the two study populations. Based on the observations made in this trial, it can be concluded that a low dose adsorbed vaccine is suitable for use in a pandemic situation.

Example 4

Reactogenicity Profile of a of Low Dose Monovalent Whole Virus Vaccine, Purified and Adsorbed on Aluminium Salt Whole influenza monovalent bulk was prepared according to Example 1 and FIG. 1 (non-trypsin method), and a monovalent influenza vaccine was formulated according to Example 2.

At the purification stage for purifying the whole virus, besides the generally applied sucrose gradient centrifugation, the selected virus rich fraction was pelleted to remove more efficiently egg-derived contaminants.

Whole virus was inactivated with formaldehyde at a concentration of 250 µg/ml (compared to the inactivation process for split vaccine which is achieved by a combination of sodium deoxycholate (NADOC) and exposure to formaldehyde at 50 µg/ml).

Once purified and inactivated, the antigen was adsorbed to a mix of aluminium hydroxide and phosphate at a concentration of 0.05 mg and 0.45 mg per dose respectively.

The purity was far superior to the purity of the whole virus adjuvanted vaccines of the past, in which plain allantoic or diluted allantoic fluid was used.

The antigen content of the whole virus was 7.5 µg/dose of A/Sydney/5/97. This dosage was selected as a worst case scenario (as the highest antigen dosage that might be selected for a pandemic monovalent vaccine) to investigate the upper limit of reactogenicity.

Based on the observations in Example 3 and the fact that whole virus is at least as immunogenic as split vaccine, it is likely that a lower antigen dose will be used.

A statistical comparison of the reactogenicity, mainly the local events observed after vaccination, was made with data on Fluarix, the SmithKline Beecham Biologicals split influenza vaccine.

The local reactions were selected for the comparison because they can be accurately measured and they are most indicative for a local reaction following an aluminium adjuvant containing vaccine.

| SCOPE | MONOVALENT NON ADSORBED SPLITVACCINE A/SYDNEY (15 µG/DOSE) | MONOVALENT NON ADSORBED SPLITVACCINE A/SYDNEY (7.5 µG/DOSE) | MONOVALENT ADSORBED SPLITVACCINE A/SYDNEY (7.5 µG/DOSE) | MONOVALENT ADSORBED WHOLE VACCINE A/SYDNEY (7.5 µG/DOSE) |
|---|---|---|---|---|
| (planned 4 × 50 n = 200) n = 196 | n = 48 | n = 49 | n = 50 | n = 48 |

Results (%)

| | | | | |
|---|---|---|---|---|
| Local and systemic reactions | 23% | 2% | 32% | 42% |
| Systemic reactions | 17% | 6% | 6% | 6% |
| Local reactions | 27% | 33% | 42% | 19% |
| Without reactions | 33% | 39% | 20% | 33% |

The Mann-Whitney U test is a statistical test for comparing 2 populations and to test the zero hypothesis that two populations of results have identical distribution functions against the alternative hypothesis that the two distribution functions differ only with respect to location (median), if at all.

The outcome of the comparison of the reactogenicity of the monovalent low dose whole virus adjuvanted vaccine to results of clinical trials on Fluarix (Trade Mark) in 1996, '97 and '99 shows that there is no significant difference at the P 0.05 level.

This observation supports the use of whole virus adjuvanted vaccine, even at an antigen dosage higher than the dosage that is sufficient to induce high protection rates against influenza.

Example 5

Immunogenicity of a Low Dose Monovalent Whole Virus Vaccine Adjuvanted with Aluminium Salts in an Unprimed Population Whole influenza virus vaccine was prepared according to Example 1 and FIG. 1 (non-trypsin method) and monovalent influenza vaccines containing different amounts of HA were formulated as described in Example 2.

The antigen used in the study was prepared from A/Singapore/1/57 (H2N2). The H2N2 subtype has not circulated in humans since 1968 and study participants $\leq 30$ years of age were immunologically naïve to the antigen. The immune status and immune response were measured as hemagglutination inhibition titers in serum samples.

The immune response at days 10 and 21 may be considered a true priming response whereas all other values represent a booster response. The results show the geometric mean titer (GMT) of the respective study group.

| H2N2 | DAY | FLUID 15 µG/DOSE | ADS. 7.5 µG/DOSE | ADS. 3.75 µG/DOSE | ADS. 1.9 µG/DOSE |
|---|---|---|---|---|---|
| $\leq 30$ years | | n = 50 | n = 47 | n = 48 | n = 51 |
| | 0 | 5 | 6 | 6 | 6 |
| | 10 | 18 | 16 | 18 | 13 |
| $2^{nd}$ vacc. → | 21 | 26 | 34 | 39 | 25 |
| | 42 | 126 | 93 | 95 | 63 |

The results presented in the table above demonstrate that a monovalent whole virus vaccine with an HA antigen content as low as 1.9 µg/dose elicits an immune response equivalent to the control group (15 µg HA/dose, no aluminium) in the unprimed study group ($\leq 30$ years, d=10, 21).

Although the HI titers are below the protective level after one immunization, a protective titer ($\geq 1:40$) is reached in all groups after two immunizations. It is not firmly established if criteria that have been developed for booster responses are fully applicable in the evaluation of a primary immune response. The value of a "non-protective" titer in case of an infection with influenza virus remains to be assessed.

These results support the use of a low-dose whole virus aluminium-adsorbed influenza vaccine for the first immunization of an unprimed population in a pandemic situation.

We claim:

1. A monovalent influenza vaccine composition comprising an influenza virus component that is a low dose of egg-derived, purified, whole influenza virus antigen from an influenza virus strain that is associated with a pandemic outbreak, or has the potential to be associated with a pandemic outbreak, in combination with a suitable adjuvant, wherein the low antigen dose is less than 15 µg of haemagglutinin per dose, and wherein the adjuvant is at least one aluminium salt.

2. The vaccine composition according to claim 1, wherein the adjuvant is a mixture of aluminium hydroxide and aluminium phosphate.

3. The vaccine composition according to claim 2, wherein the amount of aluminium phosphate exceeds the amount of aluminium hydroxide.

4. The vaccine composition according to claim 1, wherein the aluminium salts are present in the range of from about 0.4 to about 1.0 mg per vaccine dose.

5. The vaccine composition according to claim 1, wherein the low antigen dose is less than 10 µg of haemagglutinin per dose.

6. The vaccine composition according to claim 5, wherein the antigen dose is between 0.1 µg and 7.5 µg or between 1 and 5 µg of haemagglutinin per dose.

7. The vaccine composition according to claim 1, wherein the influenza virus antigen is substantially free of host cell contamination.

8. The vaccine composition according to claim 1, wherein the influenza virus component is purified by a method that includes a protease incubation step to digest non-influenza virus proteins.

9. A method for the production of an influenza vaccine for a pandemic situation, said method comprising admixing egg-derived, purified, whole influenza virus antigen from a single influenza virus strain that is associated with a pandemic outbreak or has the potential to be associated with a pandemic outbreak, with a suitable adjuvant, wherein the adjuvant is at least one aluminium salt, and providing vaccines lots that contain less than 10 µg influenza haemagglutinin antigen per dose.

10. The vaccine composition of claim 1, wherein the whole virus antigen is selected from an H2 antigen and an H5 antigen.

11. The method of claim 9, wherein the whole virus antigen is selected from an H2 antigen and an H5 antigen.

12. A method for treating a patient with a monovalent influenza vaccine composition, said method comprising the step of administering to the patient an influenza virus component that is a low dose of egg-derived, purified, whole influenza virus antigen from an influenza virus strain that is associated with a pandemic outbreak, or has the potential to be associated with a pandemic outbreak, in combination with a suitable adjuvant, wherein the low antigen dose is less than 15 µg of haemagglutinin per dose or no more than 15 µg per administered dose of vaccine, and wherein the adjuvant is at least one aluminium salt.

13. The method according to claim 12, wherein there is more than one separate administered dose, the total of which is less than 15 µg of haemagglutinin or no more than 15 µg of vaccine.

14. The vaccine composition according to claim 1, wherein the adjuvant is chosen from the group of: aluminium hydroxide and aluminium phosphate.

15. The vaccine composition according to claim 10, wherein the H2 antigen is H2N2, and the H5 antigen is H5N1.

16. The method according to claim 11, wherein the H2 antigen is H2N2, and the H5 antigen is H5N1.

17. A kit comprising a monovalent influenza vaccine composition, wherein said composition comprises an influenza virus component that is a low dose of less than 15 µg of haemagglutinin per dose, of egg-derived, purified, whole dose influenza virus antigen from an influenza virus strain that is associated with a pandemic outbreak, or has the potential to be associated with a pandemic outbreak, in combination with a suitable adjuvant, wherein said kit contains less than 10 µg influenza haemagglutinin antigen per administered dose, and wherein the adjuvant is at least one aluminium salt.

* * * * *